United States Patent [19]

Hermens

[11] Patent Number: 5,217,027
[45] Date of Patent: Jun. 8, 1993

[54] TEMPORARY CARDIAC LEAD

[75] Inventor: Martinus A. J. M. Hermens, Maastricht, Netherlands

[73] Assignee: Medtronic, Inc., Minneapolis, Minn.

[21] Appl. No.: 707,722

[22] Filed: May 30, 1991

[51] Int. Cl.$^5$ .............................................. A61N 1/04
[52] U.S. Cl. ................................. 128/784; 128/419 P
[58] Field of Search .............. 128/784, 785, 786, 419 P

[56] References Cited

U.S. PATENT DOCUMENTS

| | | | |
|---|---|---|---|
| 3,244,174 | 4/1966 | Wesbey et al. | 128/784 |
| 3,367,339 | 2/1968 | Sessions | 128/786 |
| 3,474,791 | 10/1969 | Bentov | 128/784 |
| 3,485,247 | 12/1969 | Ackerman | 128/784 |
| 3,516,412 | 6/1970 | Ackerman | 128/784 |
| 4,144,889 | 3/1980 | Tyers et al. | 128/784 |
| 4,341,226 | 7/1982 | Peters | 128/784 |
| 4,481,953 | 11/1984 | Gold et al. | 128/786 |
| 4,633,880 | 1/1987 | Osypka et al. | 128/785 |

Primary Examiner—Kyle L. Howell
Assistant Examiner—Scott M. Getzow
Attorney, Agent, or Firm—Reed A. Duthler; Harold R. Patton

[57] ABSTRACT

A temporary cardiac lead for establishing electrical contact between a body tissue and a pulse generator. The lead includes a flexible conductor having a proximal end and a distal end. The proximal end of the conductor is connected to the pulse generator. An electrode is connected to the distal end of the connector for establishing electrical contact with the body tissue. A helical coil is secured to the electrode for frictionally resisting the movement of the lead relative to the body tissue. The coil has a generally rectangular cross-section, for giving it an overall flat configuration, in order to improve the positioning of the coil within the myocardial tissue, to dispense with auxiliary accessories such as silicon rubber discs, and to reduce the size of the lead and to render it adequate for use in atrial and pediatric applications.

5 Claims, 2 Drawing Sheets

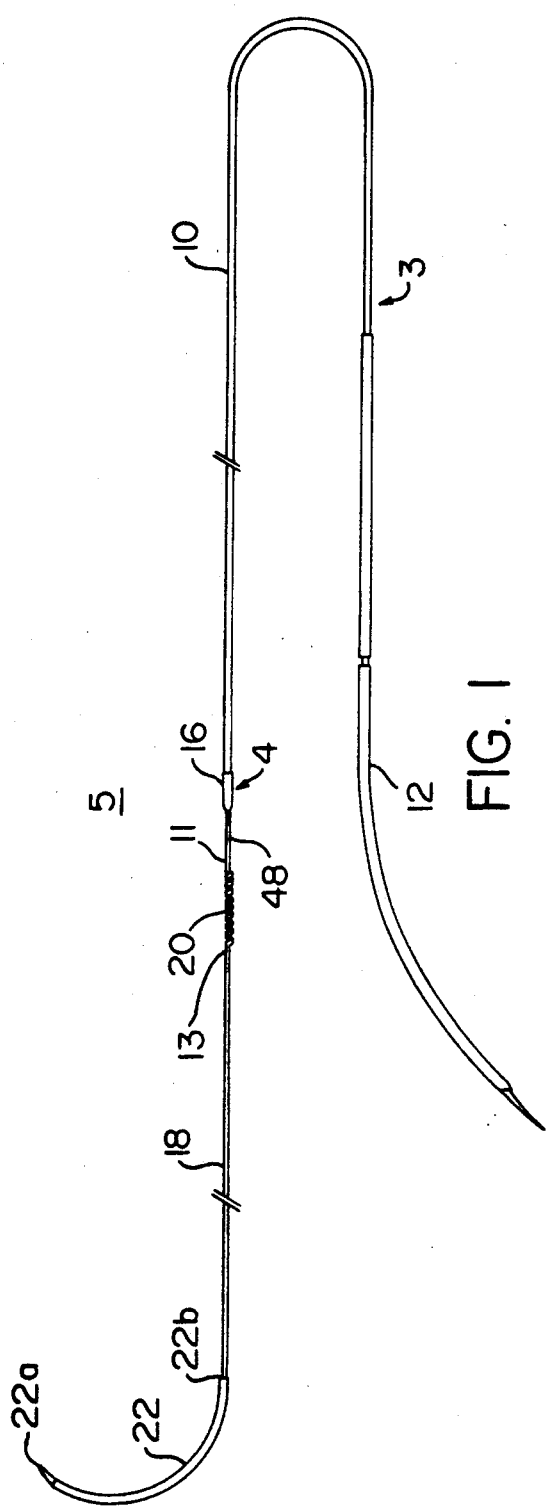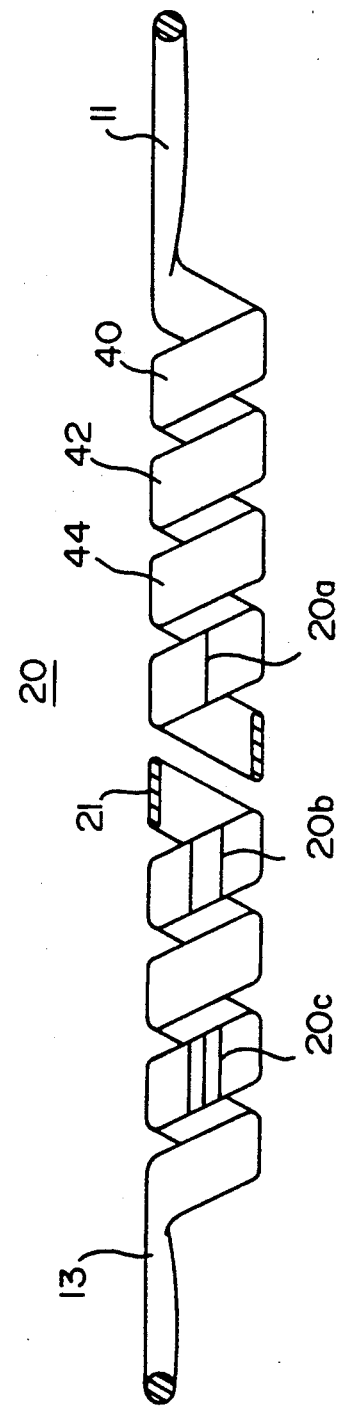

TEMPORARY CARDIAC LEAD

BACKGROUND OF THE INVENTION

1. Field of the Invention

The present invention relates to medical leads, and more particularly to a temporary cardiac lead for pediatric applications and for temporary atrial and ventricular pacing and sensing during and after cardiac surgery.

2. Background Art

Temporary cardiac leads are commonly used for pacing and sensing in that they are generally less durable than permanent leads since extended flex life is not required. It is still critical, however, that the electrodes in the temporary leads be properly affixed to the heart tissue for proper transfer of electrical signals. This electrical contact must be established in a manner which permits convenient and safe removal of the temporary leads with minimal scarring or other side effects.

Several conventional techniques have been devised to improve lead fixation and to facilitate its removal. U.S. Pat. No. 4,341,226 which issued to Peters, which is assigned to Medtronic, Inc., and which is incorporated herein by reference, is an exemplary illustration of such conventional art. The Peters patent describes a temporary lead and a corresponding insertion tool. The electrode of the temporary lead is connected to a surgical thread which extends into a helically shaped coil. The coil has a circular cross section, and is disposed at a short distance from the electrode tip. A curved needle is attached to the surgical thread for insertion into the heart tissue.

In ventricular applications, the needle is pulled through the myocardium for bringing the electrode into contact with the heart. The coil is pre-stretched before positioning by applying tension to the needle. Thereafter, as soon as the pulling force is removed, the coil tends to resiliently resume its initial pre-stretched shape. This will cause the coil to capture the tissue and to anchor itself thereto, thereby fixing the lead into position relative to the heart.

The disengagement of the coil from the myocardium and the removal of the temporary lead is accomplished by applying a force to the proximal end of the lead. This will cause the coil to stretch axially and to disengage from the myocardial tissue.

Atrial applications of the temporary lead vary from the ventricular applications described above due to the thinness of the atrial wall. In order to prevent damage to the atrial tissue, two alternative techniques are generally used in conjunction with the temporary lead. The first technique is to position the lead in a small plica on the surface of the atrium, and to hold the plica folded by means of sutures. The alternative technique is to use a silicon rubber fixation disc instead of the atrial plica. The disc retains the lead and is sutured to the atrial wall. The disc is permanently affixed to the atrial wall, and is not removed with the temporary lead. Therefore, it would be beneficial, convenient and expeditious to design a new self-anchoring temporary which does not require supplemental holding means such as plicae or retention discs.

Medtronic, Inc. is marketing the temporary lead covered by the Peters patent as part number 6500. While this temporary lead has proven to be effective in many respects, it would be desirable to improve its design in order (1) to ameliorate the coil positioning property by reducing slippage between the coil and the myocardium; (2) to dispense with auxiliary accessories such as the silicon rubber discs, thereby facilitating the lead useability in both the atrium and the ventricle; (3) to reduce the lead size for pediatric applications; and (4) to permit convenient and safe removal of the temporary lead with minimal scarring or other side effects.

Other exemplary patents in the relevant field of the invention are: U.S. Pat. Nos. 3,485,247 and 3,516,412 issued to Ackerman; U.S. Pat. No. 3,244,174 issued to Wesbey et al.; U.S. Pat. No. 3,474,791 issued to Benton; and U.S. Pat. No. 4,144,889 issued to Tyers et al.

The conventional temporary leads described in these patents have not been completely satisfactory in securing safe affixation and removal. Safe affixation and removal of temporary leads are of particular importance in pediatric applications due to the thinness of the ventricular and atrial walls of the young patient's heart. Furthermore, complications can even evolve with adult and young patients, in that lead removal might result in cardiac tamponade.

SUMMARY OF THE INVENTION

Briefly, the above and further objects and features of the present invention are realized by providing a new and improved temporary lead which can be removed safely with minimal scarring or other side effects. The temporary lead establishes electrical contact between the body tissue, such as the atrial wall and a pulse generator.

The lead includes a flexible conductor having a proximal end and a distal end. The proximal end of the conductor is connected to the pulse generator. An electrode is connected to the distal end of the connector for establishing electrical contact with the body tissue. A helical coil is secured to the electrode for frictionally resisting the movement of the lead relative to the body tissue. The coil has a generally rectangular cross-section, for giving it an overall flat construction.

Consequently, it is now possible to substantially reduce the size of the coil relative to the corresponding coil disclosed in the Peters patent. This reduction in the coil size is accompanied by a significant reduction in the overall size of the entire lead, including the electrode and the conductor, thereby rendering the lead adequate for use in atrial and pediatric applications, without the need for auxiliary accessories such as fixation discs.

The flattening of the coil presents considerable advantages not achievable by the conventional temporary leads. One such significant advantage is the down-sizing of the lead dimensions. In fact, even if the Peters lead were to be reduced in size to enable its use in atrial applications, it will not readily present the same successful results achieved by the new lead configuration. Due to its circular cross section, the helical coil in the Peters lead will not as effectively resist slippage within the cylindrical channel formed by the surgical needle. The flat turns of the new coil present significant resistive friction between the coil and the cylindrical channel, in that they tend to be wedged securely into the cardiac tissue.

BRIEF DESCRIPTION OF THE DRAWINGS

The above and other options, features and advantages of the present invention will become more apparent from the following more particular description thereof, presented in conjunction with accompanying drawings, wherein:

FIG. 1 is a plan view of the temporary cardiac lead according to the present invention;

FIG. 2 is a schematic greatly enlarged view of a helical coil for use in the lead of FIG. 1, with a portion thereof shown in cross-section to better illustrate the flat geometric design thereof;

DESCRIPTION OF THE PREFERRED EMBODIMENT

Figure 3:
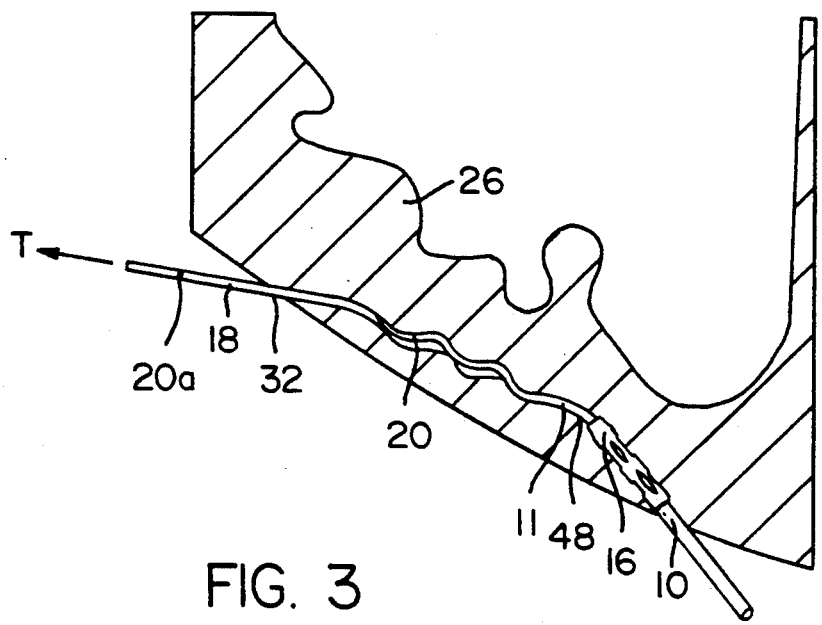
FIG. 3 is an enlarged sectional view of the myocardial tissue with tension applied to the helical coil of FIG. 2.

Referring now to the drawings and more particularly to FIG. 1 thereof, there is illustrated a temporary cardiac lead 5 which can be universally used in atrial, ventricular and pediatric applications in a safe manner, without auxiliary accessories. While the lead 5 is described herein in connection with the heart tissue, it should become apparent to those skilled in the art after reviewing the specification, that the lead 5 can be used with other body tissues and muscles for various applications beside cardiac pacing and sensing.

The lead 5 includes a proximal end 3 which extends into a metallic, electrically conductive needle 12 for connecting the lead 5 to a medical device such as a pulse generator (not shown). The needle 12 is connected to a flexible conductor (not shown) which extends along the conductive length of the lead 5, between the proximal end 3 and a distal end 4. At the distal end 4 the lead 5 is electrically connected to an electrode 16. A dielectric sheath 10 covers the exposed length of the conductor, and is made of biocompatible material such as polyethylene.

A helical coil 20 is secured at one end 11 to the electrode 16 by a surgical thread 48, by means of a crimp or by other conventional methods as described in the Peters patent. The length of the surgical thread 48 can range between 0.1 mm and 2.5 mm. At its other end 13, the coil 20 is secured to a surgical thread 18 which in turn is secured to a curved needle 22 by means of a crimp 22b. The helical coil 20 and the surgical threads 18 and 48 can be integrally formed of a single length of bio-compatible surgical thread made of a relatively inert material such as polypropylene.

As illustrated in FIG. 2, the coil 20 has a substantially rectangular cross-section 21, for giving it an overall flat configuration. As it will be described later in greater details, the flat construction of the coil 20 allows for the significant down-sizing of the lead dimensions, thus rendering it usable in pediatric and atrial applications.

Figure 4:
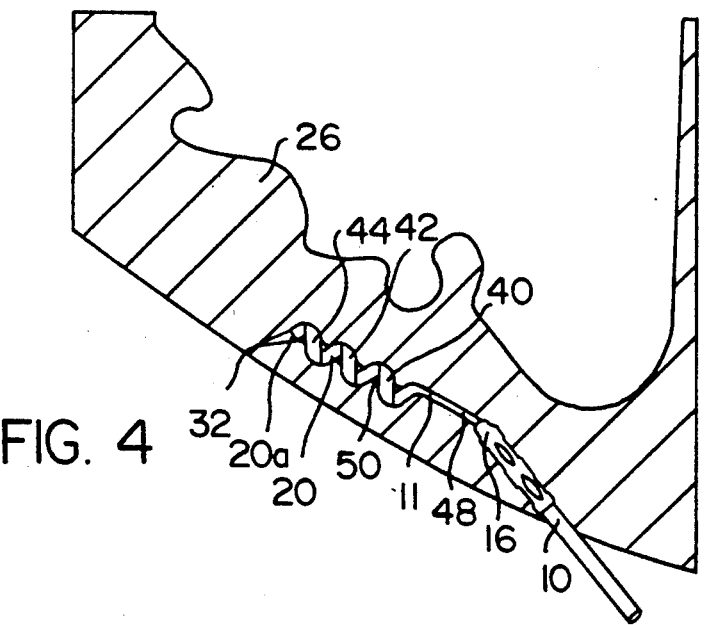
FIG. 4 is an enlarged sectional view of the myocardial tissue with the tension removed, showing the helical coil anchored to the myocardial tissue.

The needle 22 has a circular cross-section for easy insertion into the myocardial tissue. As the needle 22 perforates the heart tissue, it forms an elongated cylindrically shaped channel 50 (FIG. 4) in the tissue. The flat shape of the coil 20 allows it to be wedged frictionally into the myocardial tissue 26 and increases the effective contact area, thereby improving the fixation of the lead 5 within the cylindrical channel 50. When the tension on the needle 22 is removed, the coil 5 tends to return to its initial uncompressed state, but is prevented from reaching such a state, in that the flat turns 40, 42 and 44 of the coil 20 are firmly and frictionally wedged to the myocardial tissue 26, within the cylindrical channel 50.

While the preferred embodiment of the coil 20 is illustrated in FIG. 2, as having circular ends 11 and 13, it will become apparent to those skilled in the art that other shapes can also be selected.

In operation, the needle 22 is inserted into the myocardium 26, and is exited at location 32. The surgical thread 18 is pulled until the electrode 16 is properly positioned within part of the channel 50, in electrical contact with the myocardial tissue 26.

The tension exerted on the coil 20 by pulling the thread 18 in the direction of the arrow T, and the resistive friction between the electrode 16 and the myocardial tissue 26 cause the coil 20 to stretch and to become temporarily elongated, as shown in FIG. 3. A portion of the coil 20 is allowed to extend outside the myocardial tissue 26, at the exit location 32.

While the tension is continuously applied to the surgical thread 18, for maintaining the coil 20 in its extended and elongated state, the surgical thread 18 is severed with a conventional cutting instrument, such as a pair of surgical scissors, to remove the excess portion and to dispose of the needle 22.

In some applications it would be desirable to sever the coil 20 rather than the surgical thread 18. This will ensure that only a selected number of turns 40, 42 and 44, three in the present example are left inside the channel 50. The number of turns can be selected by the surgeon, depending on whether the lead 5 is inserted in the atrial or ventricular wall, and depending on the age and physical condition of the patient. If the lead 5 is being used for ventricular applications, it would be acceptable to leave most, if not all of the coils within the channel 50.

However, if the lead 5 is used for pediatric or atrial applications, then a lesser number of turns would be sufficient to retain the lead 5 in position within the myocardial tissue 26. In order to facilitate the selection process, identification marks, such as indentations or color coding, or other conventional coding techniques could be used. Hence, in the present example, the marking 20a is a color coded indentation to indicate visually to the surgeon that the coil 20 has been extended beyond the minimum number of turns 40, 42 and 44 required to retain and maintain the coil 20 and electrode 16 within the channel 50.

FIG. 2 shows markings 20b and 20c which provide a simple visual indication of the number of turns within the myocardium tissue 26, particularly when the coil 20 is in a stretched elongated condition (FIG. 3), and where a portion of the coil 20 is invisibly burried within the chamber 50. These markings 20b and 20c also enable the surgeon to estimate the distance between the electrode 16 and the exit location 32, for proper positioning of the electrode 16 in proper electrical contact with the myocardial tissue 26.

Once the electrode 16 is satisfactorily positioned, the surgical thread 18 is cut at the marking 20a, and the coil 20 retracts toward the electrode 16 within the chamber 50. However, the edges of the turns 40, 42 and 44 of the flat coil 20 become wedged into the tissue 26, and prevent its return to the initial unstretched position, thereby firmly affixing the electrode 16 to the tissue 26.

Therefore, the flattened construction of the coil 20 enhances the frictional mating between the coil and the myocardial tissue. The difference in shapes between the generally cylindrical channel 50 and the flat turns 40, 42 and 44 cause these turns to be anchored to the myocardial tissue 26 more firmly than the circular turns of conventional leads.

While the lead 5 is shown in FIG. 2 as having 8 turns, it is clear that a different number of turns can alternatively be selected. The overall axial length of the coil 20 can also be reduced or lengthened as appropriate for particular applications.

While a particular embodiment of the present invention has been disclosed, it is to be understood that various different modifications are possible and are contemplated within the scope and spirit of the specification, drawings, abstract, and appended claims.

What is claimed is:

1. A lead for establishing electrical contact between body tissue and a medical device, comprising:
   a flexible, insulated conductor having a proximal end and a distal end;
   means for electrically coupling the proximal end of said conductor to said medical device;
   an electrode, coupled to the distal end of said conductor;
   a length of surgical thread fixedly attached to said electrode, having a plurality of turns formed therein and having a flattened cross-section in a region including said turns; and
   a needle attached to said length of surgical thread.

2. A lead according to claim 1 wherein a segment of said surgical thread is formed into a helical coil and wherein said turns of said surgical thread comprise turns of said helical coil.

3. A led according to claim 2 wherein said surgical thread is fabricated of an inert, biocompatible plastic.

4. A lead according to claim 1 or claim 2 or claim 3 wherein said surgical thread has a generally circular cross-section other than in said region including said turns.

5. A lead according to claim 1 or claim 2 or claim 3 wherein at least one of said turns formed in said surgical thread is provided with an indicator marking.

* * * * *

UNITED STATES PATENT AND TRADEMARK OFFICE
CERTIFICATE OF CORRECTION

PATENT NO. : 5,217,027
DATED : June 8, 1993
INVENTOR(S) : Martinus A.J. M. Hermens It is certified that error appears in the above-indentified patent and that said Letters Patent is hereby corrected as shown below:

Column 6, line 12 (claim 3), the word "led" should be replaced with-- lead--.

Signed and Sealed this

Sixth Day of September, 1994

Attest:

BRUCE LEHMAN

Attesting Officer

Commissioner of Patents and Trademarks